United States Patent [19]

Bondybey et al.

[11] 4,021,217
[45] May 3, 1977

[54] DETECTING OPTICAL FIBER DEFECTS

[75] Inventors: Vladimir Edmund Bondybey, Fanwood; Louis Eugene Brus, Madison; Irene Dion Payne, Chatham; Peter Michael Rentzepis, Millington, all of N.J.

[73] Assignee: Bell Telephone Laboratories, Incorporated, Murray Hill, N.J.

[22] Filed: July 8, 1975

[21] Appl. No.: 594,013

[52] U.S. Cl. .................................. 65/13; 65/29; 65/158; 250/572; 356/200; 356/239
[51] Int. Cl.² ................ C03B 37/02; G01N 21/16
[58] Field of Search .......... 356/103, 199, 200, 237, 356/239; 250/572; 65/29, 158, 13

[56] References Cited

UNITED STATES PATENTS

| | | | |
|---|---|---|---|
| 3,478,218 | 11/1969 | Woellner et al. | 356/239 |
| 3,758,787 | 9/1973 | Sigrist | 356/104 |
| 3,759,620 | 9/1973 | Cushing et al. | 356/237 |
| 3,879,128 | 4/1975 | Presby | 356/73 |

*Primary Examiner*—Vincent P. McGraw
*Attorney, Agent, or Firm*—Peter V. D. Wilde

[57] ABSTRACT

Optical fibers in long line communication links fail often in tensile strength. Analysis of tensile properties reveals a variation in tensile strength with fiber length, pointing to uncommon structural defects randomly occurring along the fiber length. Failures occur from crack propagation at these defects. The defects can be revealed according to the invention by nondestructive monitoring during production via off-plane light scattering. A narrow light beam incident across the fiber diameter is refracted in a pattern characteristic of the fiber geometry. Variations in that pattern are produced by structural variations in the fiber or by surface contamination. The nature of the pattern change can indicate the type of defect.

3 Claims, 6 Drawing Figures

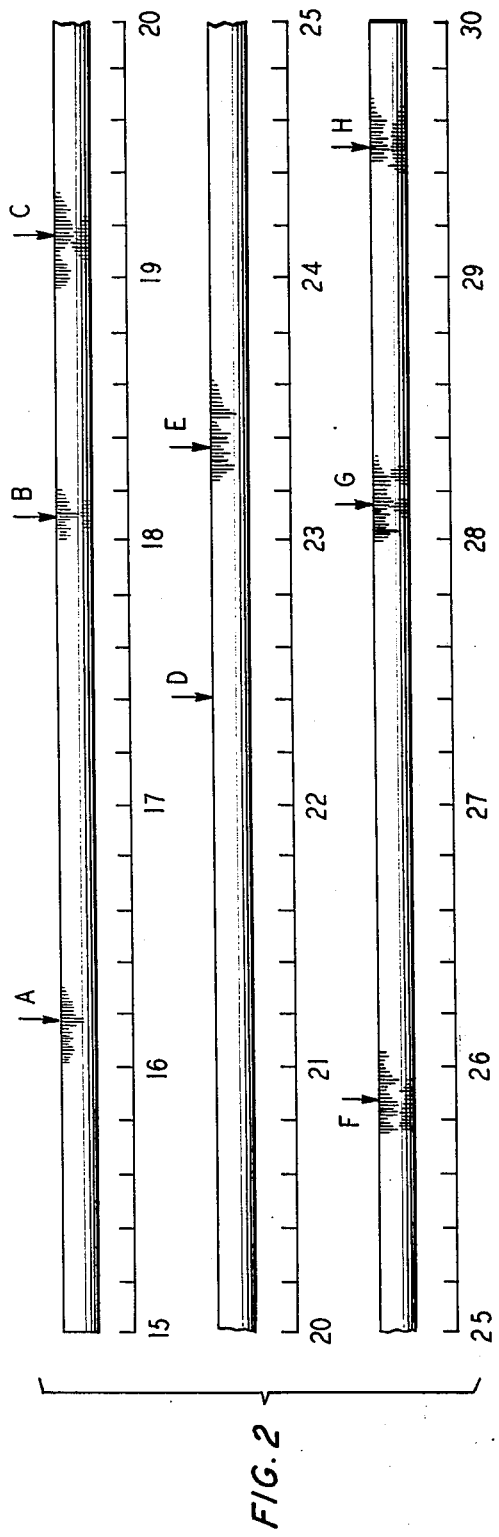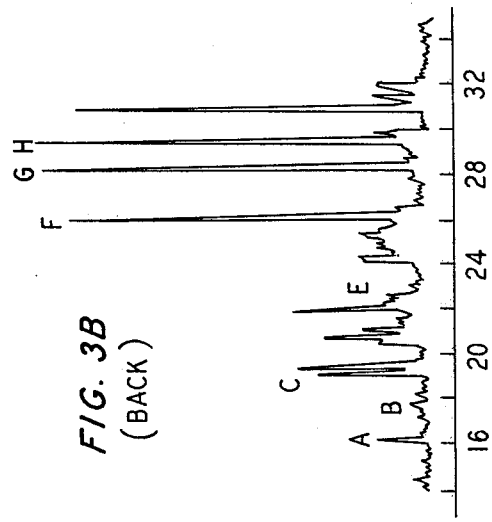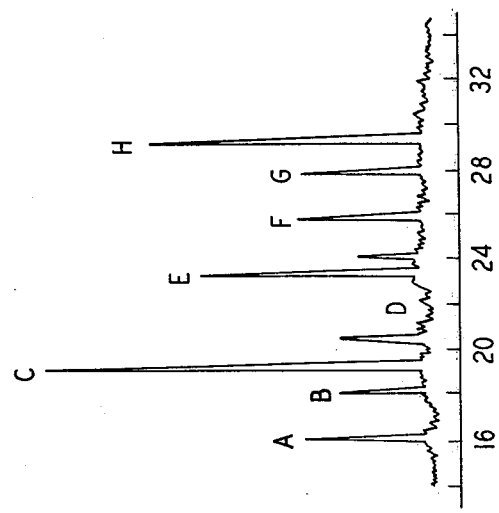

DETECTING OPTICAL FIBER DEFECTS

BACKGROUND OF THE INVENTION

The rapid development of enthusiasm for optical communications evident over the past few years is attributable to a breakthrough in the quality of glass fiber lightguides for optical transmission. Optical fiber transmission lines can now be made with extremely low loss and acceptably low mode dispersion. With appropriate coating and cabling techniques the fibers can be handled and installed. However, we have found that fibers installed in long lines (ca. 100m) have erratic tensile properties and long fiber lengths often break unexpectedly. Analysis of the tensile properties of various fibers shows an unexpected variation in tensile strength with length pointing to uncommon structural failures occurring randomly along the fiber length. Further inquiry has shown that these failures occur from crack propagation at microcracks that occur unpredictably during the fiber drawing operation. Having established that the microcracks cause the fiber breaks, we then devised a quality control system to monitor the fiber as it is drawn or processed, to reveal the presence of these defects.

The monitoring technique is based on scattering of laser light from the fiber defects. Surface defects as well as included defects are within the term "defect".

Optical scattering of laser light has been proposed as a tool for analyzing the dimensional properties of optical fibers. Marcuse and Presby, *The Bell System Technical Journal*, Vol. 54, No. 1, pp. 3–15, January, 1975, describe the use of light back scattered from a fiber to reveal distortions in the interface between the core and cladding of so-called "clad" fibers. Presby, *J. Opt. Soc. Amer.*, Vol. 64, No. 3, pp. 280–284 and Watkins, *J. Opt. Soc. Amer.*, Vol. 64, No. 3, pp. 767–772, both describe the use of scattered light for measuring fiber dimensions and refractive indices. These three techniques rely on a single optical principle and that involves the analysis of light reflected from or refracted through a curved transparent surface. The light pattern that gives the relevant data in each case is that appearing in the plane containing the light beam and normal to the axis of fiber.

SUMMARY OF THE INVENTION

The invention is a technique and corresponding apparatus for detecting structural defects in optical fibers. The technique is nondestructive, and "real time" in the sense that it can monitor fibers traveling at high rates and therefore can monitor fibers as they are produced, or processed in manufacture. It is based on analysis of off-plane light scattering from the defects.

Cracks and related defects of interest have dimensions large with respect to the wavelengths of visible light, and thus will efficiently scatter such light. Due to the typical geometries involved, the light will scatter in many directions. There is always a significant amount of scattering that occurs in the plane normal to the fiber, and that occurs whether or not a defect is present. The scattered light that we have shown to be unique to the fiber defect occurs outside the normal plane. According to the invention, this "off-plane" scattering is monitored to reveal defects that give rise to breaks in the fiber.

BRIEF DESCRIPTION OF THE DRAWING

FIG. 2 is a representation of a length of an optical fiber showing actual defects identified by the letters "A through H";

FIGS. 3A and 3B are output traces from a detector arranged to monitor fiber defects from the front and back of the fiber, respectively, with the traces related to the defects A through H of FIG. 2.

DETAILED DESCRIPTION

Figure 1A:
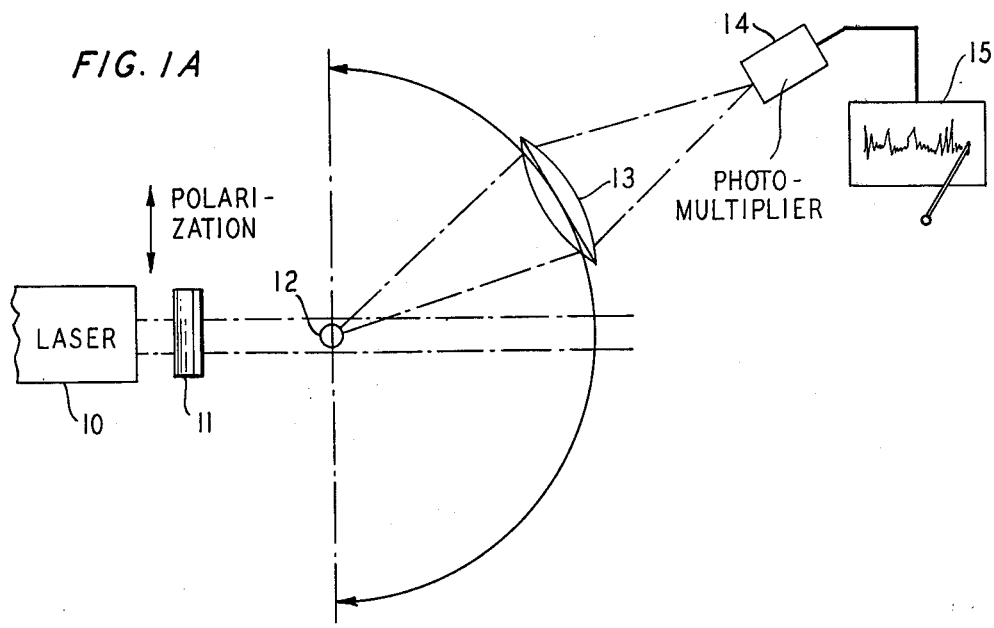
FIGS. 1A and 1B are schematic diagrams viewed from the side and top, respectively, of an apparatus for monitoring fiber defects in accordance with the invention.
Figure 1B:
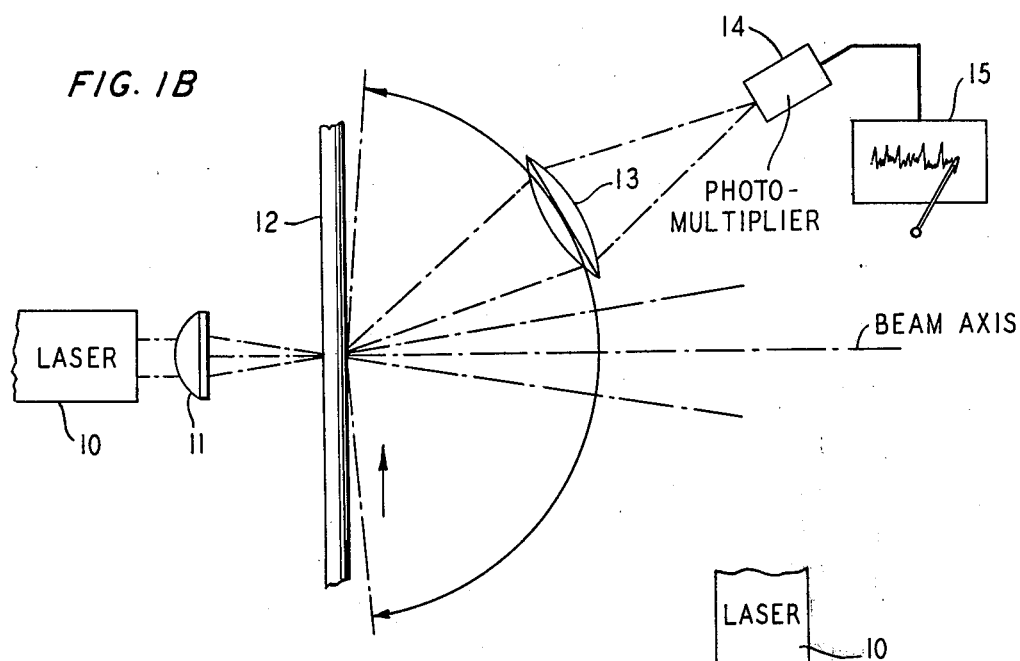

FIG. 1 shows the basic elements for obtaining the light scattered off-plane from the fiber. A source of monochromatic light 10 is directed through a lens or lens system, shown here as a cylindrical lens 11, to focus a slit of light onto the fiber 12. The beam incident on the fiber advantageously has an in-plane width large enough to include the fiber diameter so as to reveal defects over the whole fiber cross section. The out-of-plane width of the beam is correspondingly small. Since the refracted beam may scatter off defects inside as well as on both front and back surfaces of the fiber, it is preferred, but not required, to have the beam incident on the fiber polarized to minimize reflection losses. The optional polarizer is indicated schematically in FIG. 1A. Refracted light scattered off-plane is collimated by lens 13 and detected by photodetector 14. The important feature of the detector is its location off the axis of the incident beam (FIG. 1B). Off-plane light will appear more or less at any angle in the quadrant shown, although we have found that it appears typically most intense at around 15° to the beam axis. A placement angle of 5° to 70° would produce acceptable results. Viewed from the side, (FIG. 1A), the detector may be placed at any position around the plane "behind" the fiber. The useful angle is 5° to 175° from the fiber axis. A preferred placement is 30° ± 10°.

It is evident at this point that a plurality of detectors may be preferred over a single detector, although we have demonstrated that a single detector can be used effectively. Using multiple detectors one can take advantage more effectively of the fact that the pattern of radiation scattered from a defect can reveal the nature of that defect. Thus, we have been able to distinguish micro-cracks capable of causing fiber breaks from dirt particles that are removable with cleaning.

Moreover, since the cracks or other surface defects of interest typically do not scatter light isotropically, the intensity of the scattered light at a given detector location is likely to vary with the extent and orientation of the defect. If more of the radiation pattern can be analyzed, the nature, size and orientation of the defect is revealed.

There are a variety of potential responses to the detection of defects in the fiber. If the fiber is monitored as it is drawn the drawing conditions can be adjusted to eliminate the defects, or reduce their severity or number. The apparatus can be designed to mark the defect with dye or paint at a given servo signal from the photomultiplier. The most likely response in a commercial installation is to sever the fiber at or near the point of the defect and then begin a new length, or splice the fiber after eliminating the section containing the defect.

The defect detection technique of this invention was demonstrated using the following embodiment.

The apparatus was arranged as in FIG. 1. The monochromatic light source 10 was a 15 mW He-Cd$^+$ laser (4416 A). The light source can be of any wavelength capable of convenient detection. Radiation of short wavelength, even X-rays, can detect very samll defects. However, visible wavelengths are adequate and easily detected. The radiation from source 10 was polarized in the vertical plane and focused in the horizontal plane onto the fiber using a 40 mm focal length cylindrical lens. The fiber was translated through the focal region using a simple motorized translation stage at 500 microns/sec. The rate of travel of the fiber was intentionally slow to allow simple electrometer-recorder electronics for the detection operation. Accelerating the rate up to the speeds envisioned in manufacture is straightforward and involves simply the use of commonly available electronics having a shorter response. For example, if the laser is focused to a nominal waist of 20 microns on the surface of a fiber moving at 10 m/sec, then a defect small compared with the illuminated fiber length, will appear as a scattering signal with $2\mu$ sec width.

In the demonstration, the output was detected using a Philips 150 UVP photomultiplier 14, with the signal recorded on an electrometer-strip chart recorder 15. A 5.0 cm diameter lens imaged the scattered light through a glass filter (to block ambient radiation) onto the photomultiplier. The lens center was 12.5 cm from the scattering region; the lens edges just contacted the scattering plane, and the horizontal plane containing the laser beam. The fiber investigated was a Ge doped, graded index, uncoated, 110 micron diameter fiber.

The results of a sample analysis are summarized by FIGS. 2, 3A, and 3B. FIG. 2 shows a fiber with defects "A-C and E-H", located spatially along the fiber as shown. The length of this particular fiber section was about 40 mm. The electrometer recording from this fiber section is shown in FIGS. 3A which recorded the scan on the front of the fiber, and 3B, which recorded the scan with the fiber rotated 180°.

The correlation between the spatial location of the defects and the peaks occurring in the trace is evident and demonstrates the effectiveness of the detection technique. Each of the major defects seen in the illustration of FIG. 2 and denoted by letters "A-C" and "E-H", is accounted for by one of the large spikes in the front side scattering trace of FIG. 3A at the corresponding position. Conversely, part of the defect-free portion of the fiber (around 22-23 mm) denoted by letter "D", corresponds to a relatively flat portion of the scattering recording. Spike F in the scattering trace from the back of the fiber, FIG. 3B, appears to contain a contribution from both the defects at 25.9 mm and 26.2 mm. A comparison of the front and back recordings demonstrates clearly the anisotropy in the scattering signal that was explained earlier. Although each of the major spikes in FIG. 3A has a counterpart in FIG. 3B, the relative intensities vary by as much as a factor of 50. This illustrates the need for more than one detector if it is important, in a given application, to derive quantitative information.

FIG. 2 has been idealized in the sense that several small defects that appeared in the original fiber were omitted. This choice was made since in each case the defect omitted was situated on the lower hemisphere of the fiber, as seen in FIG. 1A, and the detector was located on the upper hemisphere. As noted before, these defects would not be expected to show as well in the arrangement used with the detector located in one of the other quadrants, or with multiple detectors.

Figure 4:
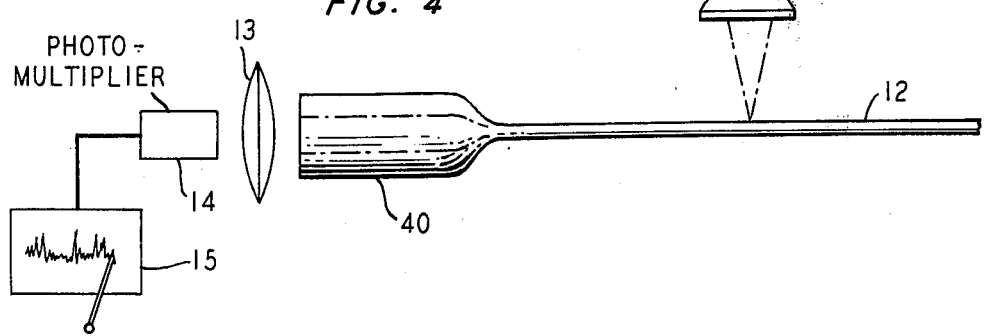
FIG. 4 is a schematic representation similar to FIG. 1 of an alternative arrangement of the detection apparatus.

If the fiber being monitored is a so-called clad fiber light that enters the core of the fiber and is scattered off-plane it is likely to become entrapped within the core because of the light guiding characteristic of this kind of fiber. This scattered radiation can still be detected but the detector is advantageously placed at the end of the fiber. An arrangement suitable for this is shown in FIG. 4. The basic elements are the same as those appearing in FIG. 1 except that the detector 14 is placed adjacent the preform 40 of the fiber as it is being drawn. Light scattered from the defect is channeled along the fiber core and along the core of the preform to the detector.

Finally, we have established that the nature of the defects, i.e., whether cracks, scratches, dirt, etc. is immaterial to the effectiveness of this detection technique.

What is claimed is:

1. A method for the manufacture of continuous lengths of optical fibers comprising the steps of:
   drawing the fiber from a heated preform at a rate in excess of 10 meters per second,
   directing a monochromatic light beam through the thickness of the drawn fiber approximately perpendicular to the axis of the fiber, the monochromatic light beam illuminating the entire width of the fiber,
   detecting the light reflected or refracted from the fiber by placing at least one light detector outside both the plane containing the beam and the fiber and the plane containing the beam and perpendicular to the fiber, and at a position 5° to 70° off the latter plane thus signaling defects in the fiber, and
   terminating the drawing of the fiber in response to light detected.

2. The method of claim 1 in which
   the light is detected at a location of 30° ± 10° from the said plane.

3. The method of claim 1 in which more than one light detector is used to signal the nature of the defect.

* * * * *